United States Patent [19]

Stolte

[11] Patent Number: 5,697,955

[45] Date of Patent: Dec. 16, 1997

[54] DEFIBRILLATOR ELECTRODES AND DATE CODE DETECTOR CIRCUIT

[75] Inventor: John F. Stolte, Burnsville, Minn.

[73] Assignee: SurVivaLink Corporation, Minneapolis, Minn.

[21] Appl. No.: 644,227

[22] Filed: May 10, 1996

[51] Int. Cl.$^6$ .............................. A61N 1/04; A61N 1/08; A61N 1/39

[52] U.S. Cl. ...................... 607/5; 607/6; 607/142; 206/438; 206/701

[58] Field of Search ...................... 607/5, 6, 8, 142, 607/129; 128/640; 206/328, 438, 459.5, 701

[56] References Cited

U.S. PATENT DOCUMENTS

| | | | |
|---|---|---|---|
| 3,685,645 | 8/1972 | Kawaguchi | 206/438 |
| 4,610,254 | 9/1986 | Morgan et al. | 607/6 |
| 4,619,265 | 10/1986 | Morgan et al. | 607/6 |
| 5,224,475 | 7/1993 | Berg et al. | 607/30 |
| 5,249,573 | 10/1993 | Fincke et al. | 607/6 |
| 5,330,526 | 7/1994 | Fincke et al. | 607/142 |
| 5,402,884 | 4/1995 | Gilman et al. | 206/701 |
| 5,405,361 | 4/1995 | Persson | 607/5 |
| 5,462,157 | 10/1995 | Freeman et al. | 206/701 |
| 5,520,683 | 5/1996 | Subramaniam et al. | 607/142 |
| 5,562,710 | 10/1996 | Olsen et al. | 607/5 |
| 5,591,213 | 1/1997 | Morgan | 607/5 |
| 5,617,853 | 4/1997 | Morgan . | |
| 5,645,571 | 7/1997 | Olson et al. . | |

FOREIGN PATENT DOCUMENTS

| | | | |
|---|---|---|---|
| WO 94/26350 | 11/1994 | WIPO | A61N 1/39 |
| WO 94/27674 | 12/1994 | WIPO | A61N 1/39 |

OTHER PUBLICATIONS

W.A.. Tacker, Jr., "Defibrillation of the Heart", Chapter 10, pp.196–222.

*Primary Examiner*—William E. Kamm
*Assistant Examiner*—Carl H. Layno
*Attorney, Agent, or Firm*—Patterson & Keough, P.A.

[57] ABSTRACT

A package of defibrillator electrodes having a date indication element and a circuit for determining a date of manufacture of medical electrodes within the package is provided. Specifically, by the circuit and package design of the present invention, the presence of a fresh package of electrodes can be detected. A circuit detectable package of medical electrodes is provided including first and second electrodes within the package. An electrical interconnection means is provided between the first and second electrodes for electrically completing a circuit connecting the lead wire of the first electrode to the lead wire of the second electrode, and includes a date identification element which when subjected to an applied voltage by way of the lead wires generates a measurable affect representative of the manufacturing period of the defibrillator electrodes. The date identification element may comprise a passive element, a value of which represents a date and can be measured. An example is a resistor of predetermined value, the value of which represents a specific manufacturing period, such as a month. A date detection circuit is provided as part of a digital control system of an automated external defibrillator to be used with a packaged pair of such electrodes. The date detection circuit determines whether the electrodes are older than the expiration period based upon the detected manufacturing period and a real time clock connected with a processor.

21 Claims, 9 Drawing Sheets

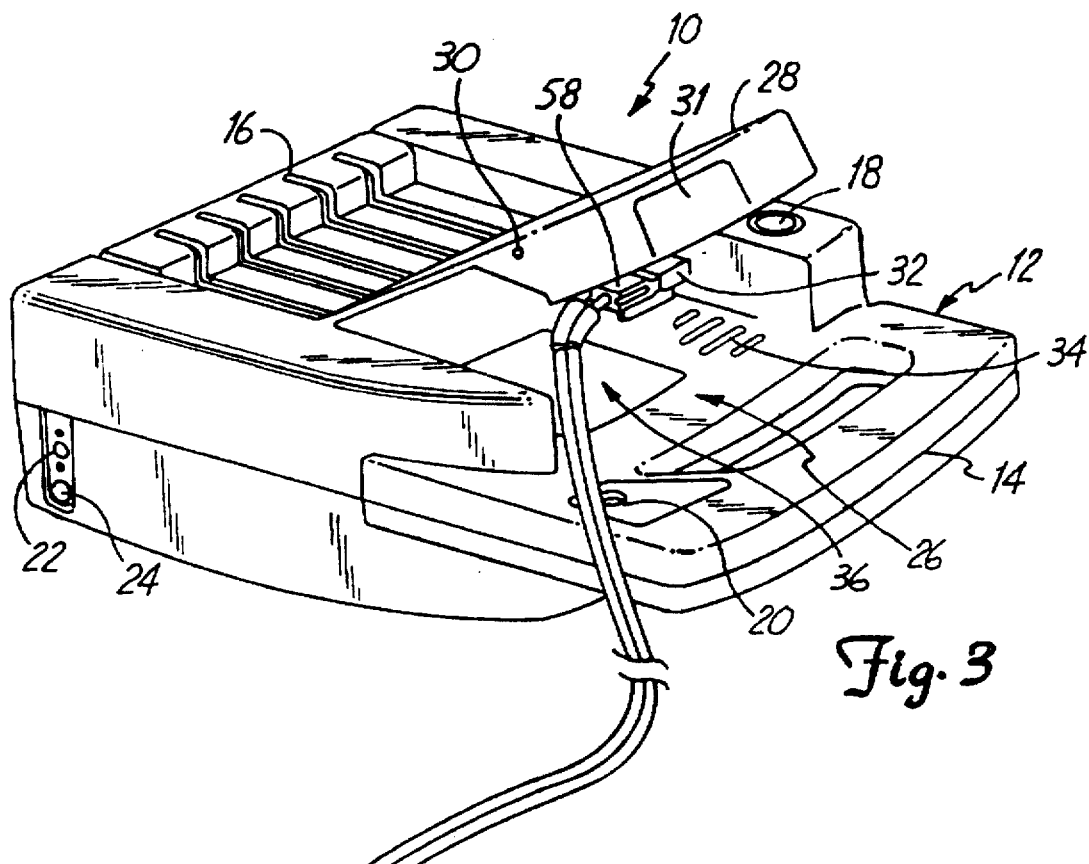
Fig. 3
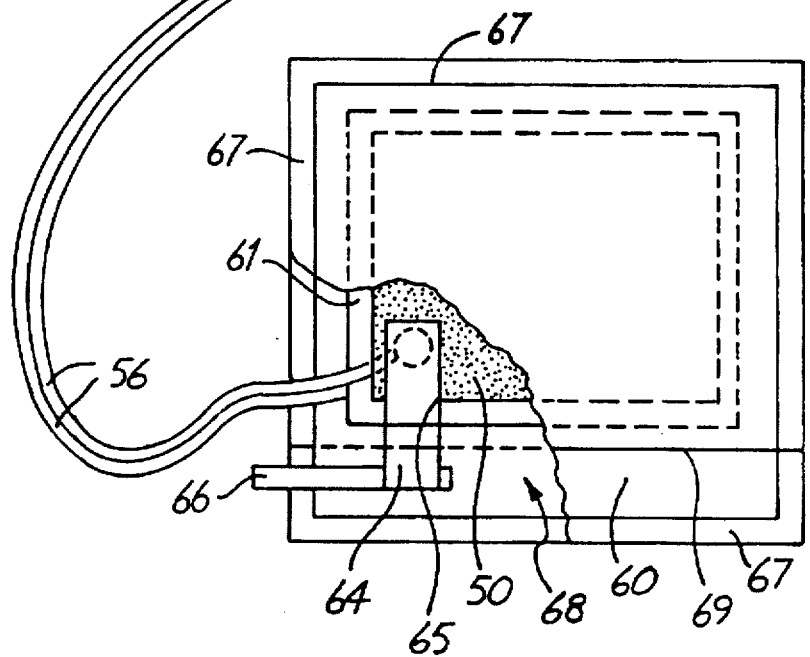

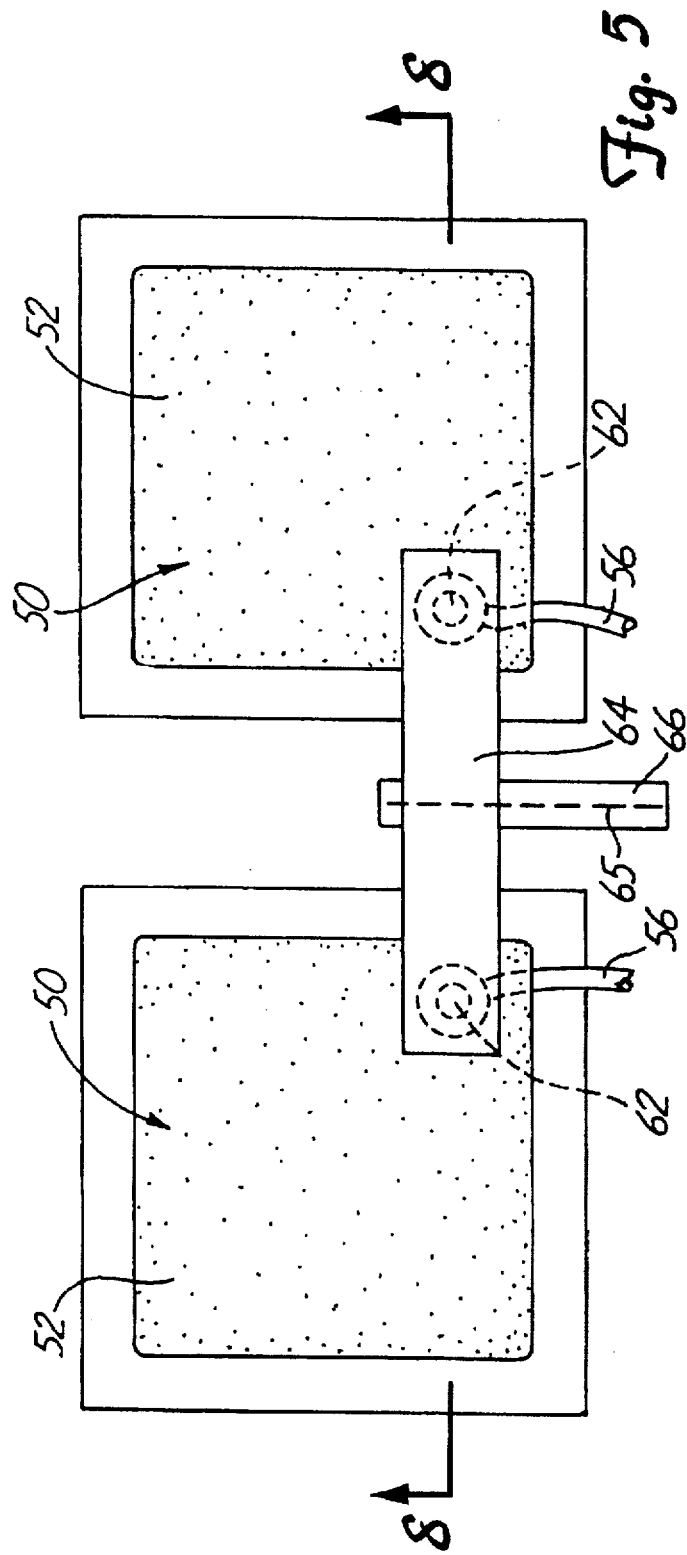
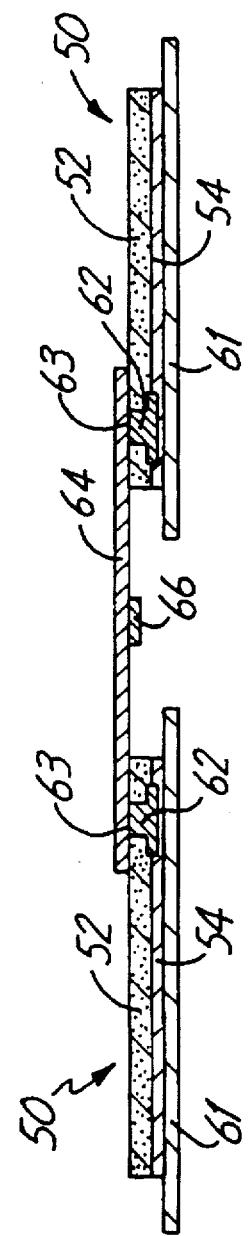

DEFIBRILLATOR ELECTRODES AND DATE CODE DETECTOR CIRCUIT

FIELD OF THE INVENTION

The present invention relates to medical electrodes usable with automated external defibrillators. In particular, the present invention relates to circuit within an automated external defibrillator for determining the freshness and status of a package of defibrillator electrodes which when in the package and connected with an automated external defibrillator completes a detection circuit as part of a self-test system for automatically and periodically testing the operational status of the defibrillator.

BACKGROUND OF THE INVENTION

Automated external defibrillators or AEDs are used by first-responder emergency medical technicians to resuscitate cardiac arrest patients. It is important that AEDs carried by these technicians be continuously operational and ready for use on a moment's notice. To help ensure a high level of confidence they will be operational when needed, AEDs should be periodically checked and tested by the technicians, and corrective maintenance performed if any faults are identified. AED's functions and components that should be periodically checked and tested, for example, include the charge state of batteries, the presence of electrodes and the ability of the device to charge and deliver defibrillation pulses.

An automated external defibrillator with self-test system has been developed and is disclosed in co-pending U.S. patent application Ser. No. 08/512,441, titled "Automated External Defibrillator with Self-Test System," which is commonly signed to the assignee of the subject application, and the entire contents of which are incorporated herein by reference. Disclosed is a defibrillator that includes a digital control system having self-test means for periodically and automatically performing self-tests of one or more defibrillator components. If a malfunctioning component is identified, the self-test means actuates an audible alarm or other maintenance indicator to alert an operator. Specifically tested functions include the presence and inter-connection of defibrillator electrodes, battery-charge state, the functionality of the high voltage circuit and the functionality of the digital control system. Some functions are self-tested daily, while others are self-tested weekly.

In order to test the presence and interconnection of defibrillator electrodes, the defibrillator electrodes must be packaged or otherwise arranged in a way to permit the testing. Specifically, it is described in the aforementioned co-pending application Ser. No. 08/512,441 that a pair of electrodes together form a part of an electric circuit through which current is run during the self-test and the impedance measured. A relatively low impedance, (e.g., less than about 10 ohms) indicates the presence of a pair of electrodes. In order for the electrodes to make up and complete an electrical circuit, both electrodes are electrically connected with one another so that a circuit can comprise the electrical lead wires of each electrode and each electrode. To do this, the electrically conducted adhesive layers of each of the pair of electrodes are affixed in a face-to-face orientation to opposite sides of a release liner within a package. The release liner is perforated with a number of apertures so that the electrodes are electrically coupled to one another within the package. A relatively low resistance electrical circuit is thereby established between the ends of the lead wires.

The above-described system effectively detects the presence of a pair of electrodes as provided in the package. An additional advantage is that the freshness of the packaged electrodes can be determined because the conductive adhesive layers increase in resistance as they dry out over time. However, a problem is that the circuit cannot distinguish between new electrodes and electrodes that have been used or tampered with and subsequently stuck back together, with or without the perforated release liner.

Medical electrode packaging is also described in U.S. Pat. No. 5,402,884 to Gilman, et al. In one embodiment, a sealed package is disclosed containing a pair of medical electrodes with the conductive adhesive layers facing one another and separated from one another by a resistive layer. A circuit can be completed through the lead wires of each electrode, through the conductive adhesive of each electrode, and through the resistive layer. Again, by monitoring resistance through the circuit, the presence of the electrodes can be detected. Also disclosed in the Gilman, et al. patent are a number of other packages for single medical electrodes. In each case, at least one conductor is provided through the package so that a circuit can be completed through the package and a portion of the conductive adhesive layer of the one electrode. These packages are disadvantageous in that they require special components in construction and in monitoring.

SUMMARY OF THE INVENTION

In accordance with the present invention, a package of defibrillator electrodes having a date indication element and a circuit for determining a date of manufacture of medical electrodes within the package is provided that overcomes the disadvantages and shortcomings of the prior art. Specifically, by the circuit and package design of the present invention, the presence of a fresh package of electrodes can be detected and distinguished from electrodes that have been used or tampered with. In other words, by the present invention, a fresh and non-opened package of electrodes can be detected.

In accordance with one aspect of the present invention, a circuit detectable package of medical electrodes is provided including first and second defibrillator electrodes within the package, each electrode comprising an electrically non-conductive flexible backing layer, a layer of electrically conductive adhesive disposed on the flexible backing layer and a lead wire extending therefrom and electrically connected with the conductive adhesive. An electrical interconnection means is provided between the first and second electrodes for electrically completing a circuit connecting the lead wire of the first electrode to the lead wire of the second electrode, and includes a date identification element which when subjected to an applied voltage by way of the lead wires generates a measurable affect representative of the manufacturing period of the defibrillator electrodes. The date identification element may comprise a passive element, a value of which represents a date and can be measured. An example is a resistor of predetermined value, the value of which represents a specific manufacturing period, such as a month. Alternatively, an active element may be used which supplies data representative of its date, for example, a read only chip.

In accordance with another aspect of the present invention, a date detection circuit is provided as part of a digital control system of an automated external defibrillator to be used with a packaged pair of electrodes electrically connected to one another by an interconnection circuit. The defibrillator includes a case, electrode terminals configured for electrical interconnection to defibrillator electrodes, a battery compartment and battery terminals in the case, the battery compartment and terminals configured for holding and electrical interconnection to one or more batteries, a high voltage circuit coupled to the battery terminals and the electrode terminals for generating defibrillation pulses and applying the pulses to the electrode terminals; and the digital control system coupled to the electrode terminals, battery terminals and the high voltage circuit. Electrode date detection means is provided for determining a manufacturing period of a packaged pair of electrodes based upon a manufacturing period represented within the intercorunection circuit of the electrodes when their lead wires are connected to the electrode terminals. In one embodiment, the electrode date detection means includes a processor means programmed with an expiration period and which determines whether the electrodes are older than the expiration period based upon the detected manufacturing period and a real time clock connected with the processor means. A maintenance indicator is preferably provided on the case which is connected with the digital control system, so that the electrode date detection means can send a signal for actuating the maintenance indicator when expired electrodes are detected. The electrode date detection means can measure an affect caused by a passive element, such as a resistor of predetermined value, within the interconnection circuit of the packaged pair of electrodes. Alternatively, the electrode date detection means can determines the date of manufacture of a packaged pair of electrodes based upon a signal generated by an active element within the interconnection circuit of the packaged pair of electrodes.

BRIEF DESCRIPTION OF THE DRAWINGS

FIG. 3 is a perspective view of the AED shown in FIG. 2, with the electrodes removed from the electrode compartment and the package partially broken away.

FIG. 5 is a detailed plan view of unpackaged electrodes positioned on release liners.

FIG. 7 is a cross-sectional view through the pair of electrodes of FIG. 5 taken along line 7—7.

DETAILED DESCRIPTION OF THE PREFERRED EMBODIMENTS

Figure 1:
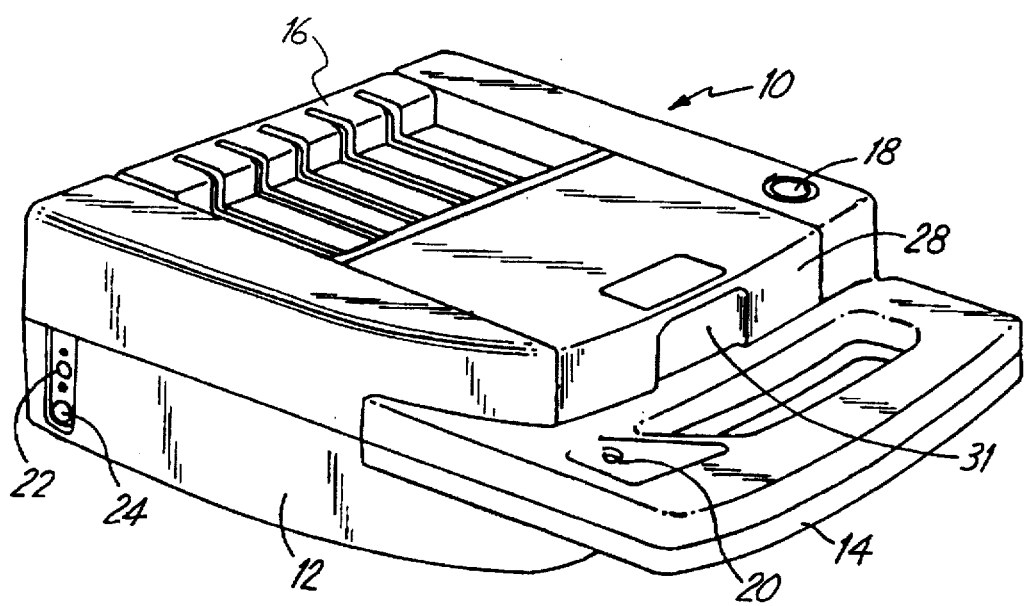
FIG. 1 is a perspective view of an automated external defibrillator (AED) in accordance with the present invention, with the electrode compartment lid closed.
Figure 2:
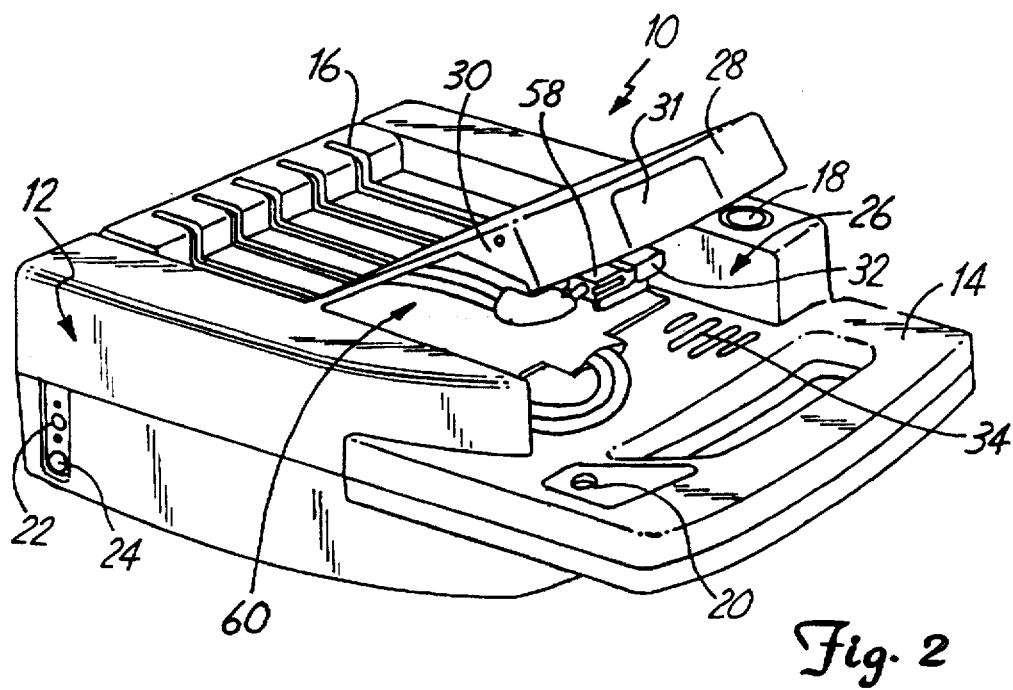
FIG. 2 is a perspective view of the AED shown in FIG. 1, with the electrode compartment lid opened and the packaged electrodes positioned therein.

A semi-automatic, automated external defibrillator (AED) 10 in accordance with the present invention is illustrated generally in FIGS. 1–3. As shown, defibrillator 10 includes a plastic case 12 with a carrying handle 14 on the top portion. A battery compartment (not visible) in the bottom portion of the defibrillator 10 is enclosed by a semi-transparent battery cover 16. An illuminable rescue switch 18, visual maintenance indicator 20, data communication port 22 and charging port 24 are located on the outside of case 12 for easy access by an operator.

Figure 4:
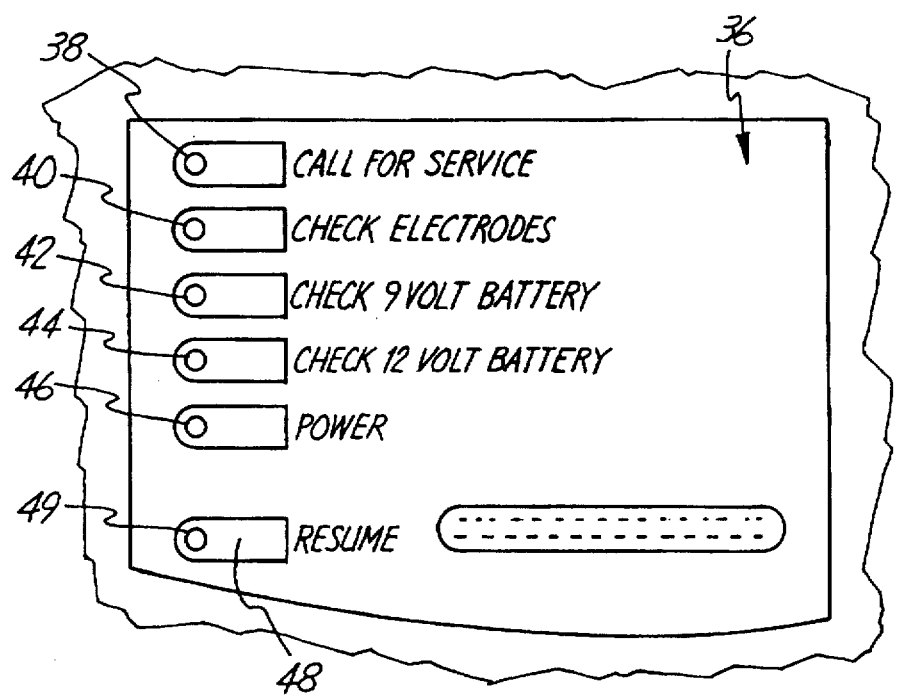
FIG. 4 is a detailed view of the diagnostic display panel in the electrode compartment.

Case 12 also includes an electrode compartment 26 between handle 14 and battery cover 16. The electrode compartment 26 is enclosed by lid 28 which is mounted to the case 12 by hinges (not visible). A friction-type releasable latch including pins 30 holds lid 28 closed when defibrillator 10 is not in use. Finger-receiving recess 31 in lid 28 is grasped to open the lid and access the electrode compartment 26. An electrode connector 32, speaker 34 and diagnostic display panel 36 are located on case 12 within electrode compartment 26. As shown in FIG. 4, diagnostic display panel 36 includes visual "Call for Service" indicator light 38, "Check Electrode" indicator light 40, "Check 9 Volt Battery" indicator light 42, "Check 12 Volt Battery" indicator light 44 and "Power" indicator light 46. Resume switch 48 and resume indicator light 49 are also located on diagnostic panel 36.

A pair of defibrillator electrodes 50 which can be used with defibrillator 10 are shown in FIGS. 3 and 5. Electrodes 50 each include a flexible polymer backing layer 52, preferably a polymeric foam, and a patient-engaging layer 54 of conductive adhesive which overlays the backing layer. A current-dispersing flexible conductive sheet (not shown) is preferably located between backing layer 52 and patient-engaging layer 54 so as to disperse current over patient engaging layer 54. The conduct sheet need not be the same size as the electrode and is preferably a homogeneous, solid, thinly deposited metallic substance, or a conductive ink. Meshes or patterns of conductive adhesives or inks may be used.

Insulated lead wires 56 extend from each electrode 50, and have a first end connected within each electrode 50 to its conductive sheet and a second end connected to a connector 58. Connector 58 is configured to releasably mate with electrode connector 32 in electrode compartment 26. Electrodes 50 are sealed within a polymer or polymer-metal laminate package 60 such as that shown in FIGS. 2 and 3. Lead wires 56 and connector 58 extend from package 60.

A first embodiment of an electrode 50 and one specific arrangement of a pair of electrodes 50 to be provided within package 60 are shown in FIGS. 5 and 7. The package design of FIG. 3 shows electrodes 50 folded against one another and provided within package 60 and as connected with defibrillator 10 by connectors 32 and 58. As shown in FIG. 7, each electrode 50 includes backing layer 52, patient-engaging layer 54 of conductive adhesive, a conductive sheet (not shown) between layers 52 and 54, and a liner 61. Liner 61 can comprise any conventional lining material such as plastic sheeting or treated papers. Both electrodes 50 may be provided together on a single liner sheet; however, for reasons set out below, other compensations would be necessary.

A lead wire 56 connects with each electrode 50. Specifically, lead wire 56 extends partially within each electrode 50, preferably between backing layer 52 and conductive adhesive layer 54. A terminal 62 is provided at the end of lead wire 56 within each electrode 50 for preferably connecting the conductive wire of lead wire 56 to the conductive sheet (not shown) between layers 52 and 54. Otherwise, the terminal 62 may directly conduct current to conductive adhesive layer 54.

In accordance with the present invention, each terminal 62 preferably extends through backing layer 52 so as to provide a conductor 63 at the surface of backing layer 52. Conductors 63 of the pair of electrodes 50, which are to be packaged together within package 60 as shown in FIG. 3, are connected together electrically by a flexible conductive connector 64. Conductive connector 64 preferably comprises a metal foil or a fine wire which can be folded for packaging and easily torn or broken, for reasons which will be evident from the description below. Moreover, connector 64 can be conventionally electrically connected to conductors 63 by conductive adhesive, heat bonding solder, or the like. Preferably, conductors 63 and conductive connector 64 are positioned and arranged, such as that illustrated in FIG. 5, so that when electrodes 50 are to be packaged within package 60, they can be folded against one another by a fold line 65 bisecting conductive connector 64. By this arrangement, an electrical circuit can be completed between lead wires 56 through terminals 62, conductors 63, and connecting conductor 64. Also, a strip of tear resistant material 66 is preferably provided that is positioned approximately at the mid-point of conductor connector 64 and which extends transverse to the direction of connector 64. Tear resistance strip 66 may comprise a plastic, paper or other non-conductive material which is tear resistant as compared to the material of conductive connector 64.

To provide electrodes 50 within package 60, the electrodes are folded toward one another along fold line 65 and positioned within a pouch type package 60, that can be conventionally made either of two sheets connected together or a single sheet folded and sealed at its edges 67. One of the sealed edges 67 accommodates the passage of lead wires 56 from package 60 by forming a small opening through the edge. Seal 67 also preferably accommodates passage of a portion of the tear resistant strip 66 from an interior portion 68 of package 60 to the outside of package 60. A tear line 69 is also provided along package 60 dividing interior portion 68 of package 60 from the rest of the inside of the package that is inhabited by the folded pair of electrodes 50. Tear line 69 may be facilitated by a line of weakening or other means for controlling package opening along tear line 69. Conductive connector 64 preferably extends within package 60 sufficiently from each electrode 50 into the package interior portion 68 so that tear resistant strip 68 also lies completely within interior portion 68.

To open package 60, a user is instructed to tear the package along tear line 69. The portion of tear resistant strip 66 extending from package 60 can be used for grabbing by the user to open the package. Otherwise, the user would simply rip along tear line 69. In tearing open package 60 along tear line 69, conductive connector 64 will be likewise torn or broken. Thus, by opening package 60, the circuit between lead wires 56 of the pair of electrodes 50 within package 60 will be broken. The provision of tear resistant strip 66 not only provides an extension for grabbing to begin opening package 60, it also ensures that conductive connector 64 will be broken during a tearing operation. As a result of this construction, the presence of an unbroken conductive connector 64 and the subsequent breaking thereof during usage of electrodes 50 can be automatically detected by defibrillator 10, as set out below, for determining the presence of fresh electrodes 50 in a ready state or in use.

Figure 8:
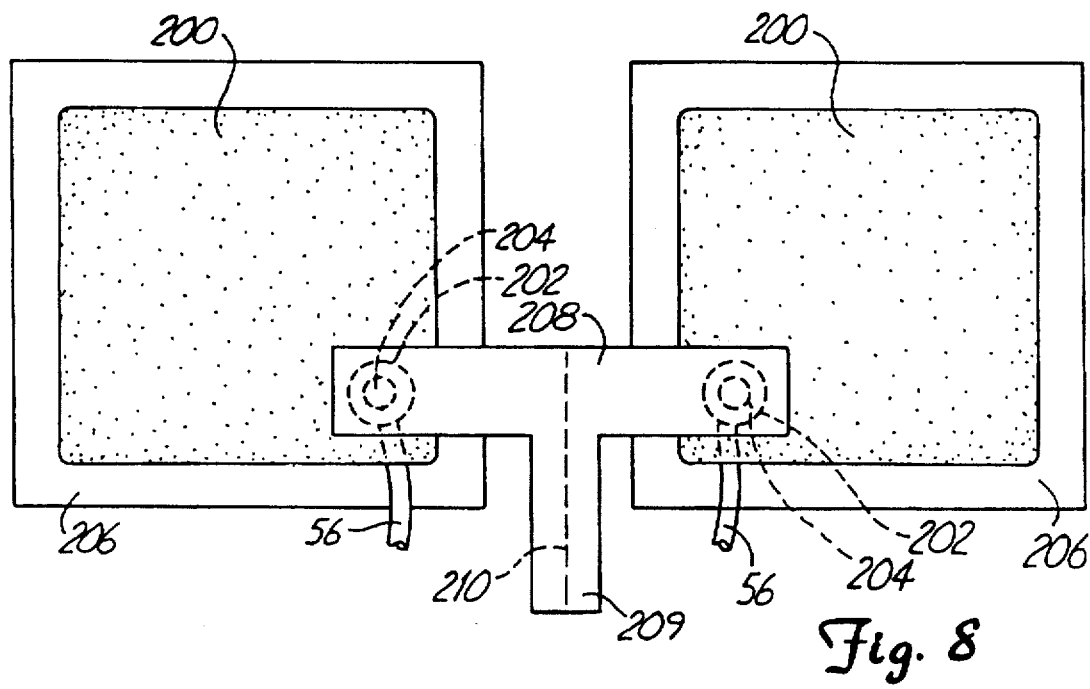
FIG. 8 is a detailed plan view of unpackaged electrodes in accordance with a second embodiment and positioned on release liners.
Figure 9:
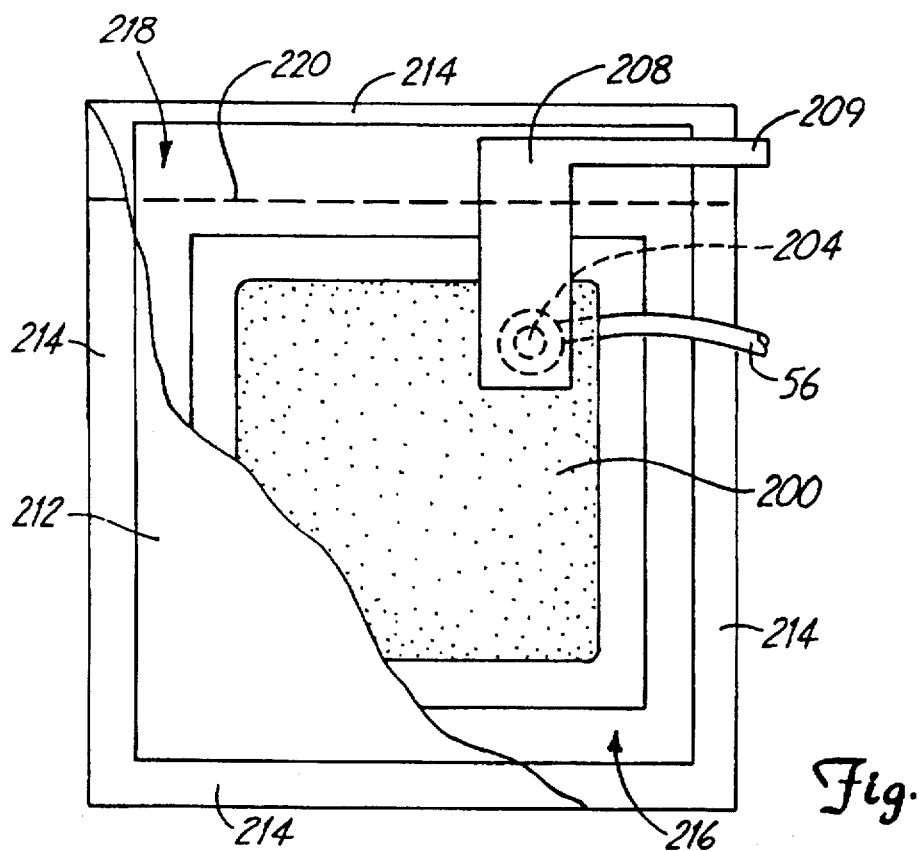
FIG. 9 is a plan view of the electrodes of FIG. 8 folded one on top of the other and provided within a package shown partially broken away.

A second embodiment of a pair of electrodes 200 is illustrated in FIGS. 8 and 9. Specifically, the construction of each electrode 200 is preferably the same as that described above including a backing layer, a patient-engaging conductive adhesive layer, and a current dispersing flexible conducting sheet therebetween. Likewise, lead wires 56 extend partially within electrodes 200 between the backing layer and the conductive adhesive layer of each electrode 200 and are preferably connected with the conductive sheets at terminals 202. Terminals 202 similarly provide conductors 204 at the surface of the backing layers of each electrode 200. Electrodes 200 are each provided on separate liners 206. As set out below, a single liner could be used. A pair of electrodes 200 are connected together by a conductive connector 208 specifically connected from one conductor 204 of one electrode 200 to the conductor 204 of another electrode 200. Again, conductors 204 can be conventionally connected to conductive connector 208 by conductive adhesive, heat bonding, solder or the like. Conductive connector 208 preferably comprises a thin metal foil. Moreover, in accordance with this embodiment, conductor connector 208 includes an extension portion 209 that is preferably integrally formed with conductive connector 208. Portion 209 extends transversely from conductive connector 208 preferably at about the center fold line 210, and extends substantially further than the edge of liners 206.

In order to provide electrodes 200 within a package 212, shown in FIG. 9, the construction and arrangement shown in FIG. 8 is folded substantially on fold line 210 so that electrodes 200 are positioned back to back with liners 206 against one another. Package 212 can be a conventional construction pouch having seal lines 214 around its periphery. Electrodes 200 are received within an electrode interior portion 216 which is divided from an interior portion 218 by a tear line 220. As above, lead wires 56 are accommodated through one of the edge seals. Likewise, portion 209 of conductive connector 208 preferably extends sufficiently such that it extends through the same package seal line 214 to facilitate opening of the package. Conductive connector 208 preferably extends within the package sufficiently from each electrode 200 into interior portion 218 so that portion 209 of conductive connector 208 lies within interior package portion 218.

To open package 212, a user would simply grasp the package at or near extension portion 209 and tear the package open along tear line 220. Extension portion 209 ensures that tearing along tear line 220 by grasping extension point 209 will tear through conductive connector 208 and break the circuit between lead wires 56. As above, the function of making and generating the circuit completed by conductive connection 208 and terminals 202 between lead wires 56 can be monitored by defibrillator 10, as set out below, for determining the presence of fresh electrodes 200 in a ready state or in use.

Figure 10:
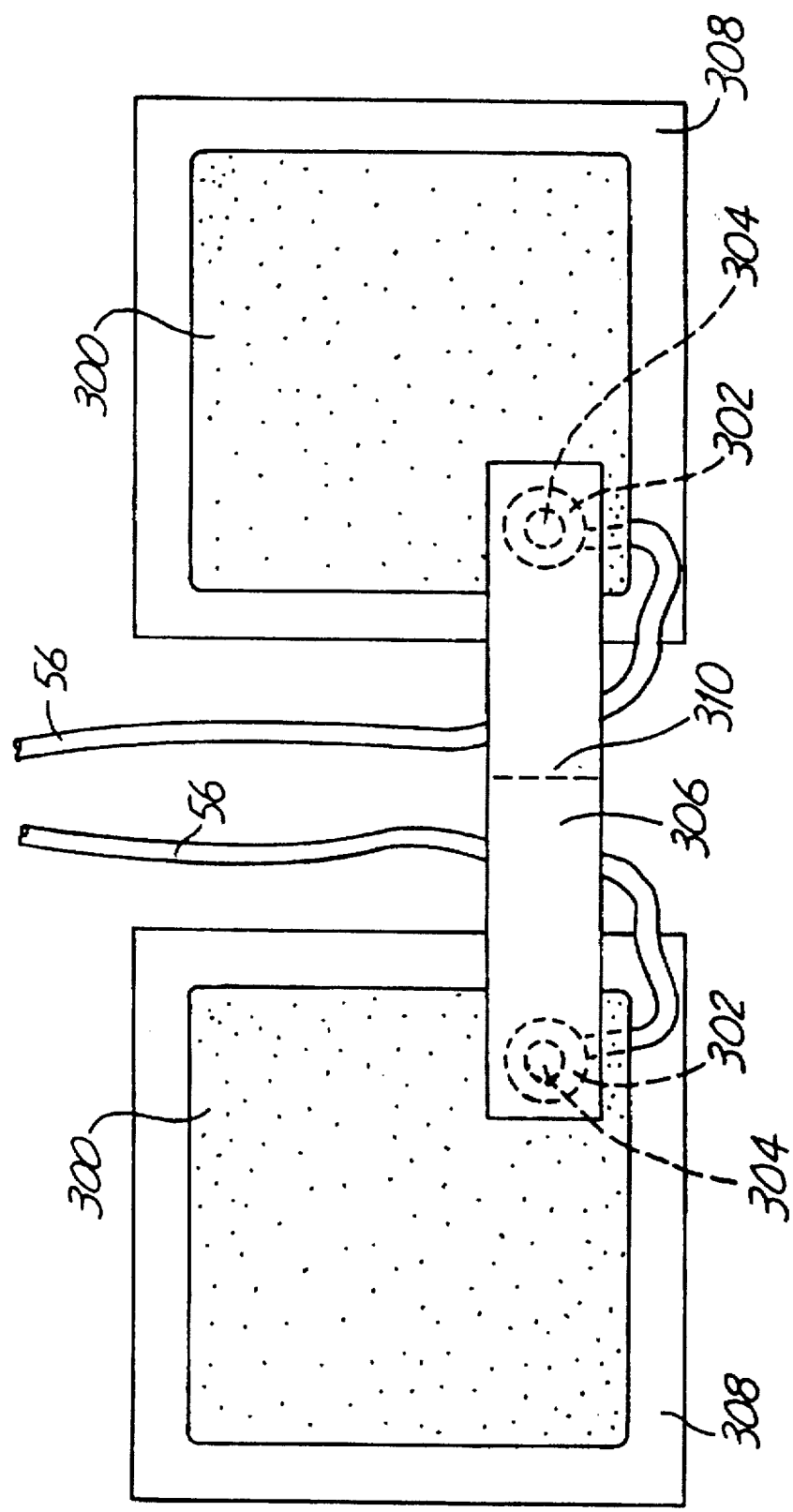
FIG. 10 is a detailed plan view of a pair of unpackaged electrodes in accordance with yet another embodiment of the present invention and positioned on release liners.
Figure 11:
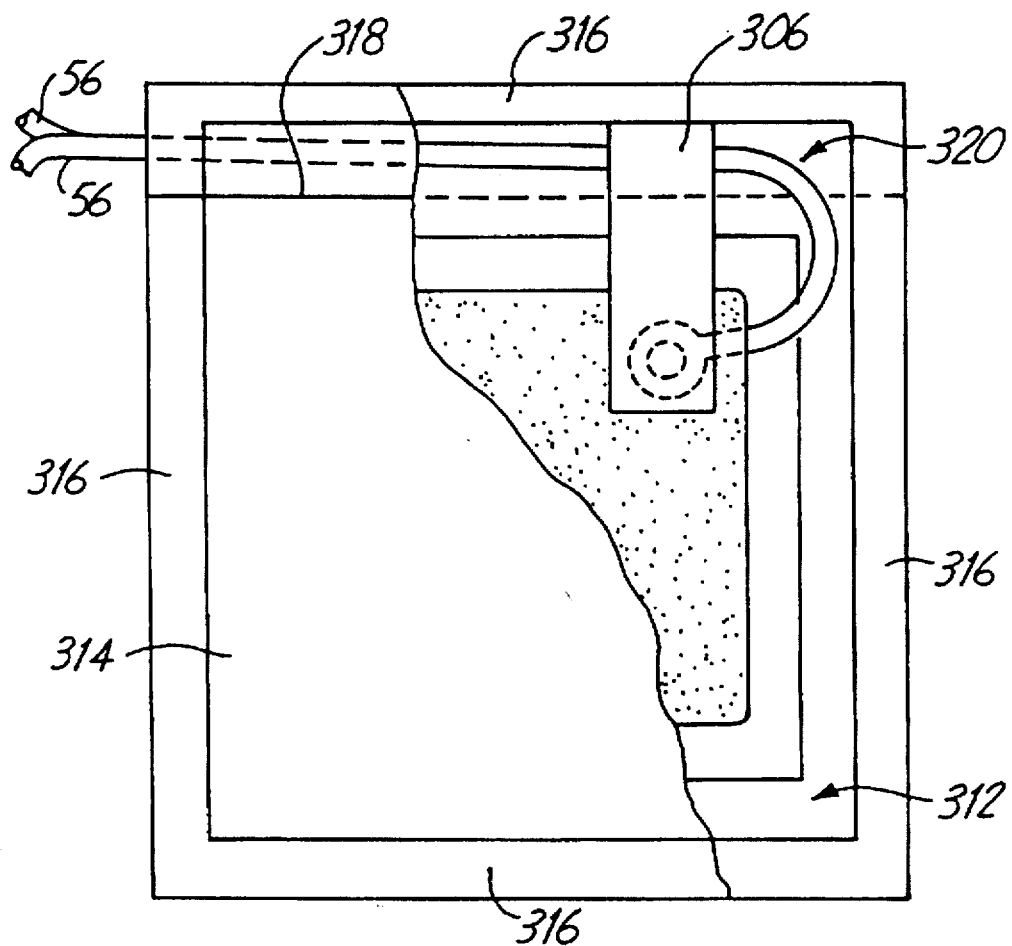
FIG. 11 is a plan view of the electrodes of FIG. 10 folded together and provided within a package shown partially broken away.

Yet another embodiment is illustrated in FIGS. 10 and 11. Electrodes 300 are provided which are similarly constructed as the aforementioned embodiments, including a backing layer, a conductive adhesive layer and a conductive sheet therebetween. Lead wires 56 are preferably connected with the conductive sheets between the backing layer and the conductive adhesive layer by terminals 302. Each terminal 302 also preferably provides a conductor 304 at the surface of the backing layer of each electrode 300. A pair of electrodes 300 are connected together by a conductive connector 306, through a conductor 304 of a terminal 302. Again, conventional connection means can be used, such as conductive adhesives, heat bonding, solder or the like. Conductive connector 306 may comprise a thin foil, a fine wire, or the like, but preferably comprises a thin foil. Each electrode 300 is also preferably provided on a separate liner 308. A fold line 310 substantially bisects conductive connector 306 so that electrodes 300 can be folded back to back with liners 308 against one another. Conductive connector 306 completes an electrical circuit for connecting lead wires 56 by way of terminals 302 and conductors 304.

The pair of electrodes 300 are positioned within an electrode receiving space 312 of package 314 which may be conventionally constructed with sealed edges 316. The interior of the package is divided by a tear line 318 into receiving space 312 and an interior portion 320.

In accordance with this embodiment, it is important that at least one of the lead wires 56 be properly threaded within the package so as to exit package 314 at one of its edge seals 316 from within interior portion 320 of package 314. Moreover, conductive connector 306 forms a loop that extends within interior portion 320 of package 314. Preferably, both of lead wires 56 pass through the loop defined by conductive connector 306 when the electrodes are positioned back to back as folded along fold line 310. More particularly, lead wires 56 pass between conductive connector 306 and an edge of a liner 308. Furthermore, conductive connector 306 is sufficiently long so that when the electrodes are folded back to back, conductive connector 306 forms the loop so as to facilitate both lead wires 56 within interior portion 320. By this embodiment, package 314 can be easily opened along tear line 318 by a user grasping lead wires 56 where they exit package 314 at edge seal 316. Then, tearing the package open along tear line 318 will also tear or break conductive connector 306. Lead wires 56, in this case, act as a tear strip facilitating easy opening of package 314. This construction is advantageous in that in a single action opens the electrode package, breaks the electrical circuit, and removes the electrodes from the package. As above, the function of making and breaking the electrical circuit completed by the connector 306 between lead wires 56 can be monitored, as set out below, for determining the presence of fresh electrodes 300 in a ready state or in use.

As an alternative construction to each of the above-described embodiments, liners 61, 206 and 308 could instead comprise a single liner to which electrodes 50, 200, and 300 respectively, are adhered. To do this, the liners would also be folded to position the electrodes within the respective packages. However, in order to provide that conductive connectors, 64, 208, and 306, respectively, extend across tear lines 69, 220 and 318, respectively, the conductive connectors must be of sufficiently greater length than the distance between the electrodes on the single liner so that when the single liners are folded, the conductive connectors will form a loop that extends sufficiently away from the folded edge of the single liner.

Figure 6:
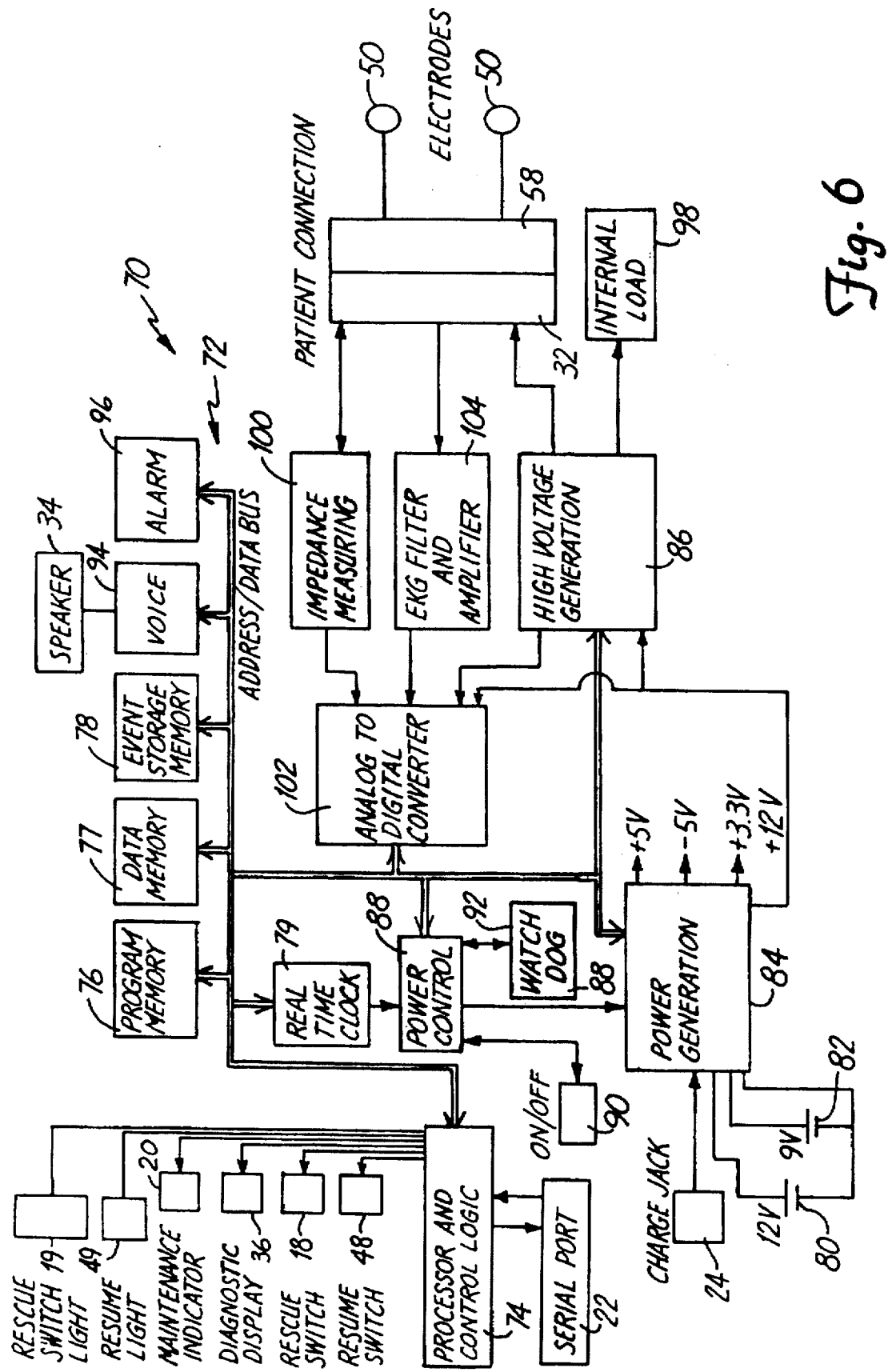
FIG. 6 is a block diagram of the electrical system of the AED shown in FIG. 1.

FIG. 6 is a block diagram of electrical system 70 of defibrillator 10. The overall operation of defibrillator 10 is controlled by a digital microprocessor-based control system 72 which includes a processor 74 interfaced to program memory 76, data memory 77, event memory 78 and real time clock 79. The operating program executed by processor 74 is stored in program memory 76. Electrical power is provided by a rechargeable twelve volt lead-acid cartridge battery 80 and a nine volt battery 82 which are removably positioned within the battery compartment and connected to power generation circuit 84. Charging port 24 is coupled to power generation circuit 84, enabling twelve volt battery 80 to be connected to a twelve volt vehicle battery (not shown) or a 120VAC charger (also not shown) and recharged while mounted within defibrillator 12. Alternatively, battery 80 can be removed from defibrillator 10 and charged in a stand-alone charger (not shown).

Power generation circuit 84 is also connected to power control circuit 88 and processor 74. Power control circuit 88 is connected to lid switch 90, watch dog timer 92, real time clock 79 and processor 74. Lid switch 90 is a magnetic read relay switch in one embodiment, and provides signals to processor 74 indicating whether lid 28 is open or closed. Data communication port 22 is coupled to processor 74 for two-way serial data transfer using an RS-232 protocol. Rescue switch 18, maintenance indicator 20, rescue switch light 19, resume switch 48, indicator lights 38, 40, 42, 44, 46 and 49 of diagnostic display panel 36, voice circuit 94 and piezoelectric audible alarm 96 are also connected to processor 74. Voice circuit 94 is connected to speaker 34. In response to voice prompt control signals from processor 74, circuit 94 and speaker 34 generate audible voice prompts.

High voltage generation circuit 86 is also connected to and controlled by processor 74. Circuits such as 86 are generally known, and disclosed, for example, in the commonly assigned Persson et al. U.S. Pat. No. 5,405,361, which is hereby incorporated by reference. In response to charge control signals provided by processor 74, high voltage generation circuit 86 is operated in a charge mode during which one set of semiconductor switches (not separately shown) cause a plurality of capacitors (also not shown), to be charged in parallel to the 12V potential supplied by power generation circuit 84. Once charged, and in response to discharge control signals provided by processor 74, high voltage generation circuit 86 is operated in a discharge mode during which the capacitors are discharged in series by another set of semiconductor switches (not separately shown) to produce the high voltage defibrillation pulses. The defibrillation pulses are applied to the patient through electrode connector 32 which is connected to the high voltage generation circuit 86.

Impedance measuring circuit 100 is connected to electrode connector 32 and real time clock 79, and is interfaced to processor 74 through analog-to-digital (A/D) converter 102. Impedance measuring circuit 100 receives a clock signal having a predetermined magnitude from clock 79, and applies the signal to electrodes 50, for example, through connector 32. The magnitude of the clock signal received back from electrodes 50 through connector 32 is monitored by impedance measuring circuit 100. An impedance signal representative of the impedance present across electrode connector 32 is then generated by circuit 100 as a function of the ratio of the magnitudes of the applied and received clock signals (i.e., the attenuation of the applied signal). For example, if electrodes 50 within an unopened package 60 are connected by conductive connector 64 and connector 58 is properly connected to connector 32 on defibrillator 10, a relatively low resistance (e.g., less than about 10 ohms) should be present across connector 32. If package 60 is opened, connector 58 is not properly connected to connector 32, or the electrodes are not properly positioned on the patient, a relatively high resistance (e.g., greater than about two hundred ohms) will be present across connector 32. The resistance across connector 32 will be between about fifty and eighty ohms when fresh electrodes 50 are properly positioned on the patient with good electrical contacts. The impedance signal representative of the impedance measured by circuit 100 is digitized by A/D converter 102 and provided to processor 74.

In addition to monitoring the electrodes, to make sure that package 60 is unopened and that connectors 58 and 32 are properly connected, it is desirable to check the freshness status of disposable electrodes 50 during the self tests. Electrodes typically have an expiration date based on their date of manufacture. As set forth in the Background section of this Application, this is because there is a tendency for the conductive adhesive to dry out over time which not only reduces the adherence of the electrodes to a patient, it also decreases the conductivity of the adhesive layer.

Figure 12:
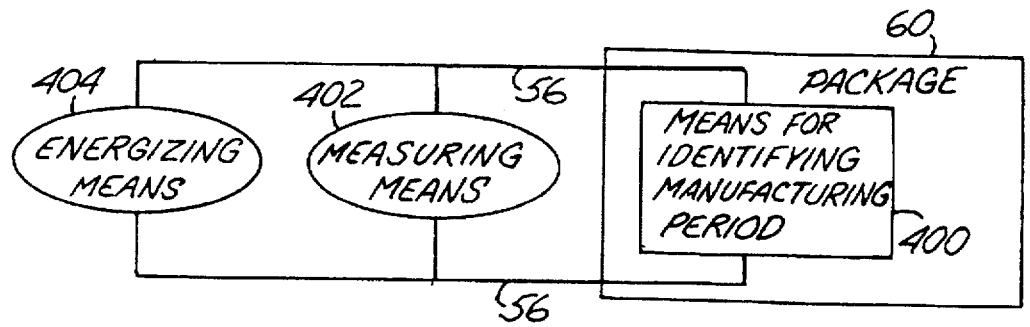
FIG. 12 is a schematic view of a general electrode date code detector circuit.

With reference to FIG. 12, a general concept is schematically illustrated for detecting the status of an electrode package of the type including the multiple embodiments described above. Specifically, the status is checked by determining the date of manufacture of the electrodes within the package that is connected to defibrillator 10 and their comparing the manufacture date with an expiration period programmed into processor 74. In other words, once the manufacturing date is ascertained, processor 74 adds to that a predetermined expiration period and compares the result to the date of testing supplied by real time clock 79.

An electrode containing package 60 is schematically illustrated in FIG. 12, however, it should be understood that any electrode packages in accordance with the present invention may be used. Within package 60, a means for identifying a manufacturing period is shown at 400. The manufacturing period may be a specific date certain, a week, a month, a year, etc. depending on the accuracy needed to determine the expiration date. Preferably, identification means 400 identifies at least the month of manufacture of the electrodes within package 60. Identification means 400 is preferably provided as part of an electrical circuit that includes a measuring means 402 and an energizing means 404 used for stimulating the circuit. Preferably, the circuit utilizes lead wires 56 for connecting to identification means 400. Measuring means 402 functions as a part of the process of determining the relevant manufacturing time as a result of the energizing of the circuit by means 404. Based upon a measured response, i.e., a signal or a change in the current or voltage, processor 74 can determine the indicated time of manufacture.

In one embodiment of the present invention, identification means 400 is an integral part of conductive connector 64, 208, or 306, which is connected between lead wires 56. Identification means may also be otherwise incorporated within package 60. Alternatively, a separate set of wires may be provided for connecting identification means 400. Furthermore, identification means 400 may be separately provided such that the separate set of wires does not have to be incorporated into the package.

Figure 13:
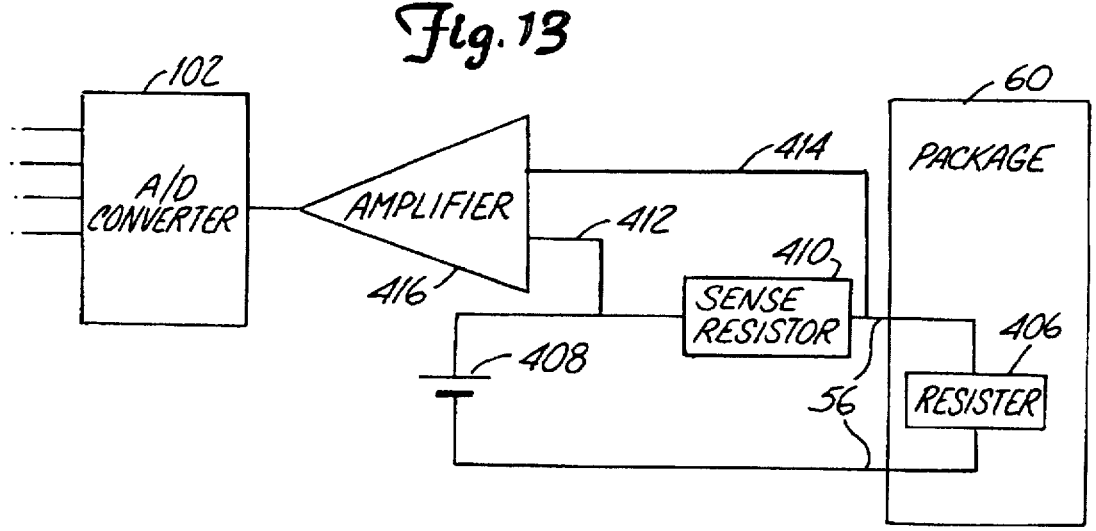
FIG. 13 is a schematic view of an electrode date code detector circuit for an electrode package including a passive component.

An example of a specific circuit that can be incorporated within the circuit o illustrated in FIG. 6 is shown in FIG. 13. This circuit comprises an implementation of the general concept described above for identifying a manufacturing period based on the presence of a passive component as identification means 400. Specifically, one example of a passive component is a resistor 406 of a predetermined resistance. The value of resistor 406 is selectively chosen to indicate a period of manufacture of the electrodes, such as the particular month. For example, if the relevant period of manufacture is to be indicated by months, twelve resistors 406 having different values would be needed, each different one to represent one month of a particular year. Preferably, each selective resistor 406 can be provided by a particularly designed conductive connector of a specific pair of electrodes. For example, the varying resistances can be provided by using packaging paper for package 60 having varying conductivity. Alternatively, a physical resistive element can be attached to package 60 using thin film resistance methods. Another alternative is to use a common resistor component and connect it through separate wires.

In the FIG. 13 circuit, the energizing means specifically comprises a voltage source 408. The measuring means comprises a sense resistor 410 of a known value, and means for measuring the voltage drop across sense resistor 410 comprising lines 412 and 414 connected through an amplifier 416 to analog to digital converter 102 (shown in FIG. 6) and processor 74. Given that the voltage of voltage source 408 is known and the value of sense resistor 410 is known, the value of the resistance across electrodes 56 (which is illustrated as 406) can be calculated using standard circuit analysis techniques. Solving for 406 the following equation is obtained: $R_E = R_s (v/v_s - 1)$ where, $R_E$ is the electrode resistance; $R_s$ is the sense resistor 410 resistance value; V is the voltage of voltage source 408; and $V_S$ is the voltage measured drop across the sense resistor 410.

Thus, having a resistor 406 with a predetermined value representing a specific month of manufacture, that month of manufacture can be determined by processor 74 based simply on the signal it receives from analog to digital converter 102 which is in turn based on the voltage drop across sense resistor 410. Moreover, processor 74, once it determines the month of manufacture, can then add to that the relevant expiration period, and make the appropriate comparison of the testing to determine freshness. If it is determined that the electrodes are beyond their expiration date, processor 74 will preferably provide a signal to both maintenance indicator light 20 and audible alarm 96. This date test is preferably conducted on the daily self-test.

Alternatively, passive component may comprise other than a resistor. Element 406 may instead comprise a capacitive element or an inductive element where the value may be determined by well known and understood methods of electronically measuring capacitance, resistance or inductance.

Figure 14:
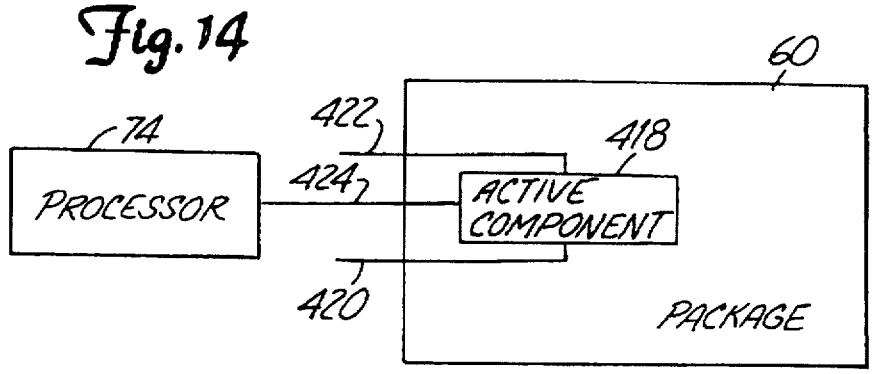
FIG. 14 is a schematic view of an electrode date code detector circuit for an electrode package including an active component.

Another example of a specific circuit that can be incorporated within the circuit of FIG. 6 is shown in FIG. 14 and comprises the implementation of the general concept of FIG. 12 but based on the presence of an active component as the identification means 400. Specifically, an active component 418 is provided within package 60 and may be provided separately from the conductive connector element of the electrode pair or may be integrally incorporated within the conductive connector. Energizing means 404 comprises a voltage source represented by lines 420 and 422. Line 424 connects active component 418 to processor 74, preferably by way of analog to digital converter 102 (not shown in FIG. 14). This circuit works on the basis that when active component 418 is connected to a voltage source, specific data is generated by active component 418 indicating the date of manufacture. The data out travels via line 424 to processor 74 which can then determine whether the electrodes within package 60 are expired or not as compared to the date of testing.

One example of an active component 418 is a read only memory chip, such as the Dallas chip DS 2400, commercially available from Dallas Semiconductor, Inc. With this type chip, the data out can include the specific date of manufacture, or any other relevant information such as manufacture identification, lot number and electrode identification. Another example is a digital sensor identifier, which provides a specific signal as the data output upon connection to the voltage source. Other known active components could also be used without departing from the spirit or scope of the present invention.

It should be noted that the electrode package described in the present invention has been described with particular reference to external defibrillators. However, it should be understood that the package of electrodes having a date indication element may be equally applicable to other devices using electrodes.

Defibrillator 10 also includes electrocardiogram (EKG) filter and amplifier 104 which is connected between electrode connector 32 and A/D converter 102. The EKG or cardiac rhythm of the patient is processed by filter and amplifier 104 in a conventional manner, and digitized by A/D converter 102 before being coupled to processor 74.

The rescue mode operation of defibrillator 10 is initiated when an operator opens lid 28 to access electrode package 60. The opening of lid 28 is detected by lid switch 90, which effectively functions as an on/off switch. In response to this action, power control circuit 88 activates power generation circuit 84 and initiates rescue mode operation of processor 74. Processor 74 then begins its rescue mode operation by switching maintenance indicator 20 to a maintenance required state (e.g., a yellow visual display in one embodiment), flashing rescue switch light 19 and the indicator lights on diagnostic display panel 36, and performing a lid opened self-test During the lid opened self-test, processor 74 checks: 1) the charge state of batteries 80 and 82, 2) the interconnection and operability of electrodes 50, 3) the state of event memory 78, 4) the functionality of real time clock 79, and 5) the functionality of A/D converter 102. The charge states of batteries 80 and 82 are checked by monitoring the voltage level signals provided by power generation circuit 84. If batteries 80 and/or 82 are determined to have a low charge, lights 44 and/or 42, respectivelyt on diagnostic display panel 36 are illuminated by processor 74. The interconnection and operability of electrodes 50 is checked by monitoring the impedance signals provided by impedance measuring circuit 100. If package 60 of electrodes 50 is missing or unplugged from connector 32, or if package 60 has been opened, processor 74 will illuminate indicator light 40 on diagnostic display panel 36. The functionality of real time clock 79 and A/D converter 102 are checked by monitoring the outputs of these circuit elements for expected signals. Diagnostic display panel light 38 is illuminated by processor 74 if faults are identified in either of clock 79 or converter 102.

If the lid opened self-test is successfully completed, processor 74 switches maintenance indicator 20 to an operational state (e.g., a black color in one embodiment), and initiates the generation of an audible "Place electrodes." voice prompt. In response to this voice prompt, and following the instructions on the inside of lid 28, the operator should remove electrode package 60 from compartment 26, tear open the package along the tear line, peel electrodes 50 from the release liners 61 and place the electrodes on the patient's chest. While this action is being performed, processor 74 monitors the impedance signals received through A/D converter 102 to determine whether the impedance across the electrodes indicates that they have been properly positioned on the patient. If the correct impedance is not measured, processor 74 initiates the generation of a "Check electrodes." voice prompt.

After detecting an impedance indicating the proper placement of electrodes 50, and without further action by the operator (i.e., automatically), processor 74 begins a first analyze sequence. In one embodiment, processor 74 collects and analyzes a nine second segment of the patient's cardiac rhythm. The cardiac rhythm analysis program executed by processor 74 is stored in program memory 76. Algorithms of the type implemented by the rhythm analysis program are generally known and disclosed, for example, in the W. A. Tacker Jr. book *Defibrillation of the Heart*, 1994.

When a shockable cardiac rhythm is detected, processor 74 begins a first charge sequence, and causes high voltage generation circuit 86 to operate in the charge mode. When the high voltage generation circuit 86 is charged, processor 74 begins a first shock sequence. The operator actuation of rescue switch 18 will then cause processor 74 to operate high voleage generation circuit 86 in the discharge mode, and results in the application of a alefibrillation pulse to the patient to complete the first series of analyze/charge/shock sequences. In one embodiment, the first defibrillation pulse delivered by defibrillator 10 has an energy content of about two hundred joules.

Following the first series of analyze/charge/shock sequences, processor 74 times out a short pause of about five seconds to allow the heart to reestablish its cardiac rhythm before beginning a second series of analyze/charge/shock sequences. The second series of analyze/charge/shock sequences is identical to the first series described above, except the energy content of the defibrillation pulse can be about two hundred joules or three hundred joules. If the second series of analyze/charge/shock sequences ends with the delivery of a defibrillation pulse, processor 74 again times out a short pause of about five second before beginning a third analyze/charge/shock sequence. A third series, and so on, is also identical to the first series, but processor 74 controls the high voltage generation circuit 86 in such a manner as to cause the defibrillation pulse delivered upon the actuation of rescue switch 18 to have an energy content of about three hundred and sixty joules.

Throughout the analyze, charge and shock sequences, processor 74 monitors the impedance present across connector 32 to determine whether electrodes 50 remain properly positioned on the patient. If the monitored impedance is out of range (e.g., too high if the electrodes have come off the patient, or too low if shorted), processor 74 initiates the generation of a "Check Electrodes." voice prompt, and causes high voltage generation circuit 86 to discharge any charge that may be present through internal load 98. Rescue mode operation will resume when processor 74 determines that the electrodes have been properly repositioned on the patient.

Processor 74 initiates and performs a lid closed self-test when lid 28 is closed following rescue mode operation of defibrillator 10. During the lid closed self-test, processor 74 performs a comprehensive check of the status and functionality of defibrillator 10, including: 1) the state of event memory 78; 2) the functionality of real time clock 79; 3) the functionality of A/D converter 102; 4) the functionality of program memory 76, data memory 77 and event memory 78; 5) the charge state of batteries 80 and 82; and 6) the interconnection and operability of electrodes 50. The state of event memory 78, the state of batteries 80 and 82, the interconnection and operability of electrodes 50, and the functionality of clock 79 and A/D converter 102 are checked in a manner identical to that described above with reference to the lid opened self-test. Light 38 on diagnostic display panel 36 is illuminated (when lid 28 is subsequently opened), and maintenance indicator 20 is switched to its maintenance required state by processor 74 if faults are identified during the lid closed self-test or during the daily self-test as will be described below. No audible alarms are actuated if faults are identified that are expected such as in the charge state of batteries 80 or 82 or the interconnection or functionality of electrodes 50 during the lid closed self test or during the daily self-test. However, alarm 96 is actuated by processor 74 if other faults are identified during the lid opened self test.

A daily self-test is initiated and performed by processor 74 at a predetermined time each day (i.e., every tweny-four hours). During the daily self-test processor 74 performs all the component check operations described above that are performed during the lid opened and lid closed self-tests. In addition to illuminating the appropriate lights on diagnostic display panel 36, processor 74 switches maintenance indicator 20 to its maintenance required state and activates alarm 96 if faults are identified during the daily self-test.

Processor 74 also initiates and performs a weekly self-test at a predetermined time one day each week. During the weekly self-test processor 74 performs all the component check operations described above that are performed during the daily self-test. In addition, processor 74 causes high voltage generation circuit 86 to sequentially operate in its charge and discharge modes, with the charge being dumped to the internal load 98. While the high voltage generation circuit 86 is operating in the charge mode, processor 74 monitors the time required to charge the capacitors and the capacitor voltage. A fault is identified if either is out of nominal conditions. Maintenance indicator 20 and alarm 96 are actuated in the manner described above if any faults are identified during the weekly self-test.

Upon the completion of each lid opened, lid closed, daily and weekly self-test, processor 74 causes a record of the self-test to be stored in event memory 78. Each stored record includes data representative of the date and time of the test and the results of the test. The test results are recorded in the form of a code or other description indicating whether all the functions, components and component status states passed the test, or indicating the nature of any identified faults. In one embodiment, only the records of the ten most recently Although the present invention has been described with reference to preferred embodiments, those skilled in the art will recognized that changes can be made in form and detail without departing from the spirit and scope of the invention.

What is claimed is:

1. An automated external defibrillator for use with a packaged pair of electrodes electrically connected to one another by an interconnection circuit and including lead wires with connectors extending from the package, the defibrillator comprising:

a case;

electrode terminals configured for electrical interconnection to defibrillator electrodes;

a battery compartment and battery terminals in the case, the battery compartment and terminals configured for holding and electrical interconnection to one or more batteries;

a high voltage circuit coupled to the battery terminals and the electrode terminals for generating defibrillation pulses and applying the pulses to the electrode terminals; and a digital control system coupled to the electrode terminals, battery terminals and the high voltage circuit, including:

electrode date detection means for determining a manufacturing period of a packaged pair of electrodes based upon a manufacturing period represented within the interconnection circuit of the electrodes when their lead wires are connected to said electrode terminals.

2. The defibrillator of claim 1, wherein said electrode date detection means includes a processor means programmed with an expiration period and which determines whether the electrodes are older than the expiration period based upon the detected manufacturing period and a real time clock connected with the processor means.

3. The defibrillator of claim 2, further including a maintenance indicator on the case which is connected with said digital control system, and said electrode date detection means further includes a signal means for actuating the maintenance indicator when expired electrodes are detected.

4. The defibrillator of claim 3, wherein said electrode date detection means further comprises a passive element within the interconnection circuit of the packaged pair of electrodes.

5. The defibrillator of claim 4, wherein said passive element is a resistor.

6. The defibrillator of claim 3, wherein said electrode date detection means further comprises an active element within the interconnection circuit of the packaged pair of electrodes.

7. An automated external defibrillator including a packaged pair of electrodes electrically connected to one another by an interconnection circuit and including lead wires with connectors extending from the package, the defibrillator comprising:

a case;

electrode terminals electrically interconnected to the connectors of the defibrillator electrodes;

a battery compartment and battery terminals in the case, the battery compartment and terminals configured for holding and electrical interconnection to one or more batteries;

a high voltage circuit coupled to the battery terminals and the electrode terminals for generating defibrillation pulses and applying the pulses to the electrode terminals; and a digital control system coupled to the electrode terminals, battery terminals and the high voltage circuit, including:

electrode date detection means for determining a manufacturing period of the packaged pair of electrodes based upon a manufacturing period represented within the interconnection circuit of the electrodes.

8. The defibrillator of claim 7, wherein said electrode date detection means includes a processor means programmed with an expiration period and which determines whether the electrodes are older than the expiration period based upon the detected manufacturing period and a real time clock connected with the processor means.

9. The defibrillator of claim 8, further including a maintenance indicator on the case which is connected with said digital control system, and said electrode date detection means further includes a signal means for actuating the maintenance indicator when expired electrodes are detected.

10. The defibrillator of claim 9, wherein the interconnection circuit of the packaged pair of electrodes includes a passive element which represents a manufacturing period and which when subjected to an applied voltage through the lead wires generated from the digital control system causes an effect that is measured by said electrode date detection means and from which the date of manufacture is determined.

11. The defibrillator of claim 10, wherein said passive element comprises a resistor having a predetermined value representative of a manufacturing period and said electrode date detection means measures the value of the resistor and based on the measured value determines the period of manufacture.

12. The defibrillator of claim 9, wherein the interconnection circuit of the packaged pair of electrodes includes an active element which generates data representative of a manufacturing period when subjected to an applied voltage through the lead wires generated from the digital control system and said electrode date detection means determines the date of manufacture of the packaged pair of electrodes based upon the generated data.

13. A package defining a pouch having an interior cavity including first and second electrodes within said interior cavity, each electrode comprising an electrically nonconductive flexible backing layer, a layer of electrically conductive adhesive disposed on said flexible backing layer and a lead wire extending therefrom and electrically connected with said conductive adhesive, wherein an electrical interconnection means is provided between said first and second electrodes for electrically completing a circuit connecting the lead wire of said first electrode to the lead wire of said second electrode, said electrical interconnection means including a date identification element which when subjected to an applied voltage by way of the lead wires generates a measurable affect representative of the manufacturing period of the electrodes.

14. The package of electrodes of claim 13, wherein the date identification element comprises a passive element which represents a manufacturing period.

15. The package of electrodes of claim 14, wherein said passive element comprises a resistor having a predetermined value representative of a manufacturing period.

16. The package of electrodes of claim 13, wherein the date identification element comprises an active element which generates data representative of a manufacturing period when subjected to the applied voltage.

17. The package of electrodes of claim 16, wherein said active element comprises a read only chip.

18. A packaged electrode pair having a date indication element comprising:

a package having an inner chamber and a plurality of edge seams;

first and second electrodes stored in the inner chamber of the package; and an interconnection member for electrically connecting the first and second electrodes, wherein the interconnection member includes a date identification element.

19. The packaged electrode pair of claim 18, wherein each of the first and second electrodes have an electrically nonconductive backing layer, a layer of electrically conductive adhesive disposed on the backing layer and a lead wire extending therefrom and electrically connected with the conductive adhesive.

20. The packaged electrode pair of claim 19 wherein the date identification element comprises a resistor having a predetermined value representative of a manufacturing period.

21. The packaged electrode pair of claim 19, wherein the date identification element comprises an active element which generates data representative of a manufacturing period when subjected to an externally applied voltage.

* * * * *

UNITED STATES PATENT AND TRADEMARK OFFICE
CERTIFICATE OF CORRECTION

PATENT NO. : 5,697,955
DATED : December 16, 1997
INVENTOR(S) : John F. Stolte

It is certified that error appears in the above-indentified patent and that said Letters Patent is hereby corrected as shown below:

Column 1, line 7, please add the word "a" before the word "circuit".

Column 1, line 32, please change the word "signed" to the word "assigned".

Column 3, line 11 and 12, please change the word "intercorunection" to the word "interconnection".

Column 3, line 27, please change the word "determines" to the word "determine".

Column 9, line 19, please change the word "their" to the word "then".

Column 9, line 56, please delete the letter "o" between the words "circuit" and "illustrated".

Column 12, line 17, please change the word "voleage" to the word "voltage".

Column 12, line 18, please change the word "alefibrillation" to the word "defibrillation".

Column 12, line 33, please change the word "second" to the word "seconds".

UNITED STATES PATENT AND TRADEMARK OFFICE
CERTIFICATE OF CORRECTION

PATENT NO. : 5,697,955
DATED : December 16, 1997
INVENTOR(S) : John F. Stolte

It is certified that error appears in the above-indentified patent and that said Letters Patent is hereby corrected as shown below:

Column 12, line 46, please change the word "Electrodes" to the word "electrodes".

Column 13, line 42, please delete the word "recently" and add the phrase "recent results are stored.".

Column 13, line 45, please change the word "recognized" to the word "recognize".

Column 13, line 58, please change the word "and" to the word "an".

Column 14, line 38, please change the word "and" to the word "an".

Signed and Sealed this

Sixteenth Day of June, 1998

BRUCE LEHMAN

*Attest:*

*Attesting Officer*  *Commissioner of Patents and Trademarks*